(12) United States Patent
Shriver

(10) Patent No.: US 8,771,305 B2
(45) Date of Patent: Jul. 8, 2014

(54) LATERAL INTRAVASCULAR EXCISION/INCISION DEVICES

(76) Inventor: Edgar Louis Shriver, Aventura, FL (US)

(*) Notice: Subject to any disclaimer, the term of this patent is extended or adjusted under 35 U.S.C. 154(b) by 1094 days.

(21) Appl. No.: 12/268,835

(22) Filed: Nov. 11, 2008

(65) Prior Publication Data

US 2010/0121258 A1   May 13, 2010

(51) Int. Cl.
*A61B 17/14* (2006.01)
*A61B 17/32* (2006.01)

(52) U.S. Cl.
USPC ............................................. 606/180

(58) Field of Classification Search
USPC .......... 606/159, 167, 170, 171, 180; 600/564; 604/22
See application file for complete search history.

(56) References Cited

U.S. PATENT DOCUMENTS

| | | | | |
|---|---|---|---|---|
| 3,320,957 | A * | 5/1967 | Sokolik | 606/180 |
| 6,500,187 | B1 * | 12/2002 | Petersen | 606/167 |
| 2003/0055444 | A1 * | 3/2003 | Evans et al. | 606/159 |
| 2004/0167428 | A1 * | 8/2004 | Quick et al. | 600/564 |
| 2005/0090848 | A1 * | 4/2005 | Adams | 606/180 |
| 2006/0111733 | A1 | 5/2006 | Shriver | |

* cited by examiner

*Primary Examiner* — Katherine M Shi

(57) ABSTRACT

A lateral incision catheter device is described which has a first shell formed as a hollow semi-spherical surface of hard, rigid material with circumference approximately that of half a true circle, and having a longitudinal axis longer or shorter than that of a true circle, and the shell edge on each side of the longitudinal axis being a cutting surface, and with a first catheter passing through and being bonded to the first shell on the longitudinal axis of the first shell near the distal end of the first catheter and a second shell essentially the same as the first but slightly larger and bonded to the distal end of a slightly larger catheter so as to surround the first and having an opening on the longitudinal axis for the distal end of first catheter to enter and thus serve as the axis for both concentric shells. A practitioner advances the lateral incision catheter to a pre-selected site in the lumen of a blood vessel, rotates one or both catheters to properly position the shells radially then rotates the first catheter and second catheter in opposite directions so the cutting surfaces of the shell edges engage adjacent tissue to cut out and remove a section of patient's lumen wall between the closing shell edges, and after the first and the second shells have rotated about 180 degrees they constitute a substantially closed container holding the excised portion of lumen wall which may be removed from the blood vessel by retraction of the lateral incision catheter. The device may be introduced through and used in a hemostatic guiding catheter which prevents blood from escaping though the opening on the lumen wall after the opening is made.

7 Claims, 11 Drawing Sheets

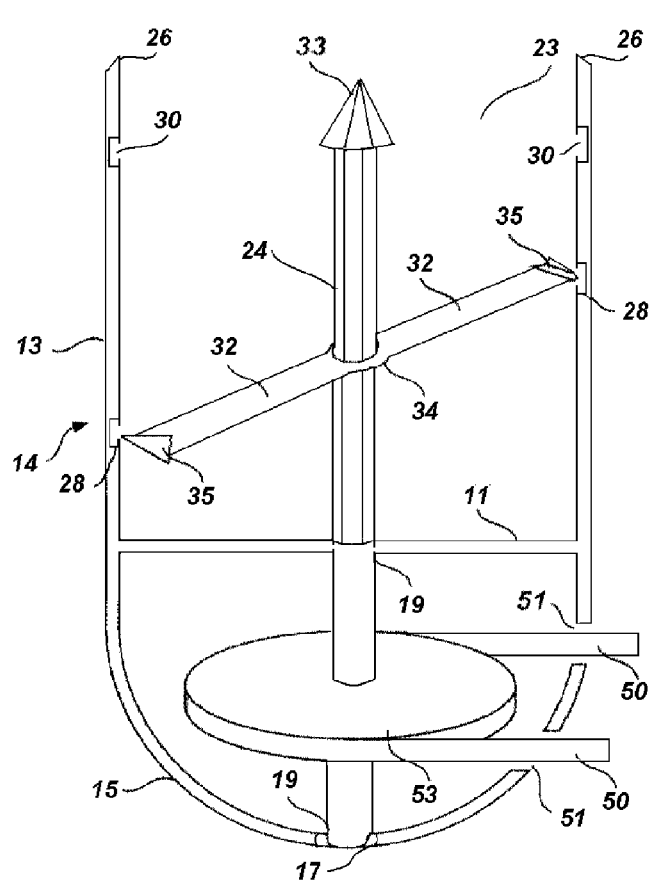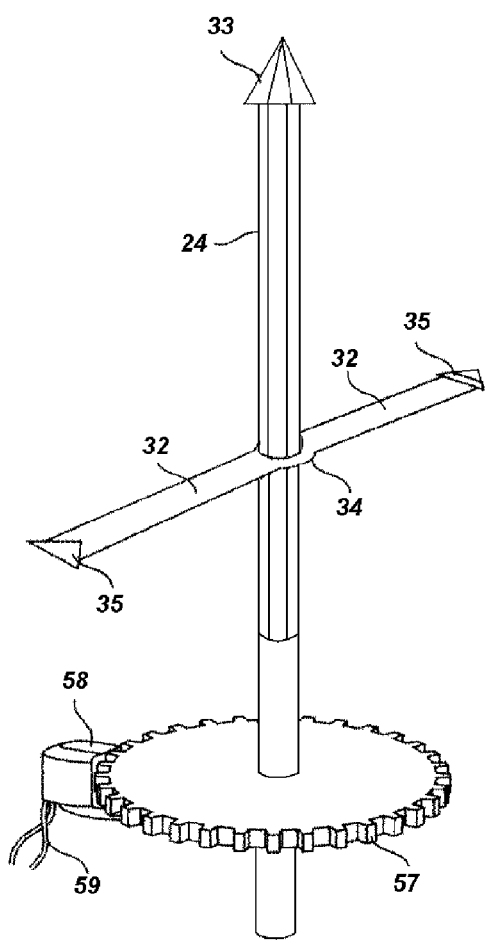
Fig. 3A                    Fig. 3B

LATERAL INTRAVASCULAR EXCISION/INCISION DEVICES

FIELD OF THE INVENTION

The field of the invention generally relates to catheters, balloons, and cutting tools for percutaneously performing arteriotomies or other percutaneous procedures within a patient.

BACKGROUND

Revascularization restores blood flow in vessels by either going around or going through an occlusion that is restricting flow. A bypass graft redirects a supply of blood upstream of the occlusion site, around the occlusion, and delivers it to a site downstream of the occlusion site. Highly evasive surgery, conducted by cutting from outside the body to reach the site where the bypass graft is placed, is used to place a bypass graft. Existing percutaneous methods of revascularization, thus, go through the occlusion rather than around it.

Percutaneous entry to reach occluded arteries in the body is accomplished at locations where an artery is close to the surface of the skin, e.g., in the femoral artery of the groin. When the femoral artery is being accessed, a guiding catheter is inserted in the femoral artery and advanced toward either the coronary or peripheral arteries. The device(s) for accomplishing revascularization are then advanced through the guiding catheter and to the site of the occlusion by a practitioner. A common device for opening an occlusion is a balloon on a catheter, advanced through the guiding catheter, then entering the occlusion and being inflated to push the occlusion open. A more recent technique adds a bare or drug-eluting stent of wire mesh around the balloon to keep the occluded area propped open after the balloon is removed. The guiding catheter may also be used as the passageway for advancing devices other than balloons and stents that are used for removing an occlusion. These devices generally include mechanical and electrical means for removing calcified, thrombus-filled, or other types of occlusions within the vessel.

SUMMARY OF THE INVENTION

Embodiments of the invention provide devices, systems, and methods for percutaneous surgery, including percutaneous bypass graft surgery. In some embodiments, a lateral incision device is positioned at a target site within the body by a practitioner. Once there, the practitioner may control the device to stop or divert fluid flow in the target vessel and core or otherwise create an opening in the wall of the resident vessel. The fluid flow in the vessel may be stopped by balloons near or at the distal end of the multi-luminal device. The coring or other creation of an opening may be performed laterally into the resident vessel wall in an area sealed by the expanded balloons. Various coring or penetrating devices may be used in the device. These include cup-shaped coring devices, rotating blades, and rotating shells. Thermal, UV or other penetrating devices may be suitable as well. These cutting devices may be extended from the device by the practitioner during a procedure and may be retracted back into the lateral incision device by the practitioner after the coring is complete.

In addition to these, various other embodiments of this lateral incision device, related systems, and applicable methods are also possible. Thus, many methods, systems, and devices may be employed to perform related percutaneous lateral bypass incisions consistent with embodiments of the invention.

BRIEF DESCRIPTION OF THE DRAWINGS

Embodiments are provided, by way of example only, with reference to the accompanying schematic drawings in which corresponding reference symbols indicate corresponding parts, where:

FIG. 3A shows a cross-sectional perspective view of the cup taken along line 3A-3A of FIG. 2D, in accord with embodiments of the invention;

FIG. 3B shows components of the cup that may be used to rotate the shaft and the cutting blades of FIG. 3A;

DETAILED DESCRIPTION

The following description should be read with reference to the drawings, in which elements in different drawings are intended to be numbered in like fashion. The drawings, which are not necessarily to scale, depict selected embodiments and are not intended to limit the scope of the invention. Examples of construction, dimensions, materials, and manufacturing processes are provided for various elements but merely as a reflection of current manufacturing practice. The examples provided have suitable variations and alternatives, which may be utilized now and in the future.

Figure 1A:
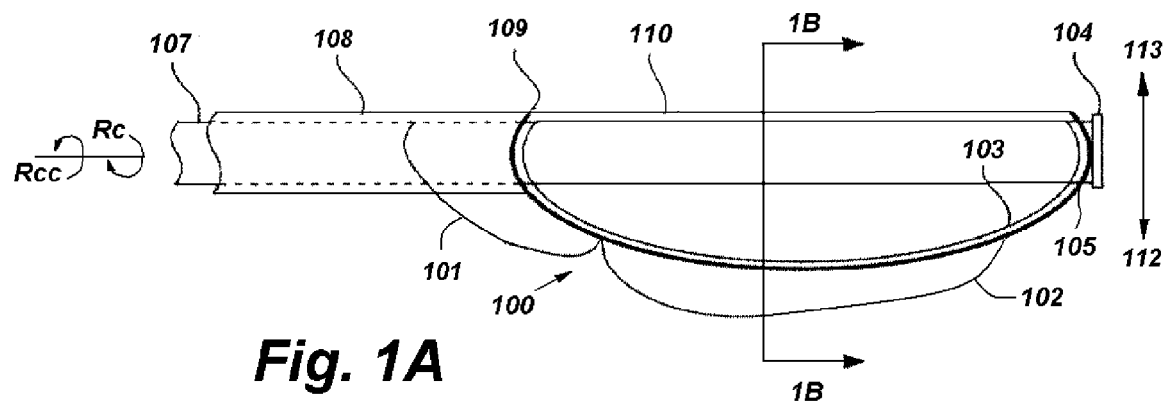
FIG. 1A is a side view of a lateral incision catheter in accord with an embodiment of the invention.

FIG. 1A shows a side view of a lateral incision shell catheter 100 according to embodiments of the invention. This lateral incision shell catheter 100 may be used to cut or core an incision at a target site of a lumen of a patient in which the catheter is being guided through. At a target site, one or more coring shells may be used to cut out and remove sections of the patient's lumen wall adjacent to the coring shells. As can be seen in FIG. 1A, the lateral incision catheter 100 may include an inner first catheter 107 surrounded by an outer, second catheter 108. In this embodiment, the inner first catheter 107 is shown with a coring shell 103 near its distal end and the outer second catheter 108 is shown with a coring shell 109 at its distal end.

The illustrations of the lateral incision catheter 100, as well as the other devices depicted within the drawings, rarely employ ghost-lines (dashed-lines) to illustrate components that would be hidden from view in the particular figures. Ghost-lines have been avoided for ease of illustration and to better illustrate the internal components of the devices depicted herein. For example, the inner coring shell 103 and the inner first catheter 107 of FIG. 1A would not ordinarily be visible from this vantage point. However, for clarity, and ease of illustration, they have been drawn with solid lines rather than in ghost-line format.

The edges of the coring shells 103 and 109 may include one or more cutting surfaces, which may be used to cut a target area of an adjacent lumen wall at a target site. When the first shell 103 rotates about its longitudinal axis, a cutting surface 110 of the rotating first coring shell 103 may cut through an adjacent lumen wall. In a preferred implementation, the first inner catheter 107 and thus the first coring shell 103, may be rotated with respect to the second catheter 108 while the second coring shell 109, will generally remain stationary during a procedure. In other words, the outer catheter may be positioned at a target site such that the outer shell generally engages the target site. Now positioned against the target site, the inner coring shell may be rotated within the outer shell and engage and cut the target vessel.

In addition, as the inner first rotating catheter 107 is rotated by a practitioner in a first direction the outer rotating catheter 108 may be rotated in an opposing direction to core an adjacent lumen wall. Rotation of the inner catheter 107 and the outer shell catheter 108 may also be independently controlled by a practitioner. Thus, rotation of the first shell 103 and the second shell 109 may each be independently controlled as well. For example, as discussed above, the second rotating catheter 108 may be used to properly position the second shell 109 radially with respect to a site on the artery. Next, by rotating the first rotating catheter 107, the first shell 103 may rotate with respect to the second shell 109. In some implementations, rotation of the first shell 103 and the second shell 109 may be concentric about a common axis A-A, although this need not be the case.

The cutting surface 110, which may be on one or both sides, may be a serrated blade and may be coated with a lubricious material as an aid in cutting through tissue. Other cutting methodologies may be used as well. The second coring shell 109 may also be pushed or drawn to the target site prior to coring the target with the coring shell 103. A vacuum may be drawn through the inner catheter 107 and/or the coring shell may be pushed upwards by the expansion of balloon 102. In each of these instances, the outer coring shell 109 may be snuggly secured to the target site, thereby permitting the inner coring shell 103 to core target tissue at the target site as with a drum and drumhead.

Figure 1B:
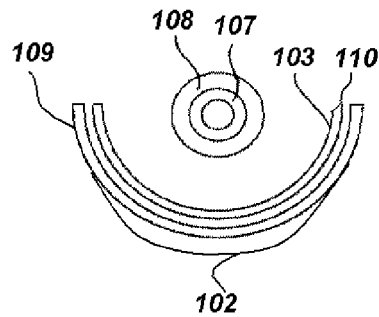
FIG. 1B is a cross-sectional view taken along line 1B-1B of FIG. 1A.

FIG. 1B is a cross-sectional view taken along line 1B-1B of FIG. 1A. The drawings are not to scale and spacing between elements is exaggerated for clarity. Preferably, the first shell 103 may fully rotate 360 degrees or more with respect to the second shell 109 in a clockwise-direction $R_C$ or a counter-clockwise direction $R_{CC}$. When the first shell 103 is rotated approximately 180 degrees with respect to second shell 109, a substantially closed container or vessel may be formed for holding excised tissue. This closed container may be retracted from the target site to remove the excised tissue from the body.

As noted above, a balloon 102 may be attached to the second shell 109. When inflated, the balloon 102 may expand in a direction 112 against a surface (e.g., the inner surface of a hemostatic guiding catheter) so as to urge the outer shell 109 in a direction 113 toward the target site. In one implementation, the balloon 101 may be adhesively attached to the outside surface of the second shell 109. A second balloon 102 may be further located on the outer surface of the second shell 109 and the outer catheter 108. When inflated the second balloon 102 may hold the second shell 109 against a surface of a guiding catheter in which the incision catheters reside. The inflatable balloons 101 and 102 may be fabricated, for example, from biocompatible materials such as polyurethane, nylon elastomers or other thermoplastic elastomers.

The first and second catheters 107, 108 may each have a flexible elongated shaft that has a generally circular circumference. The shell 103 may be attached to the first catheter 107, for example, by brazing, welding (including laser), adhesive, or other bonding means.

As can be seen in FIG. 1A the first catheter 107 may pass through an opening 105 in the second shell 109. A rotating flange 104 may also securely cap the distal end of the first catheter 107 to be vacuum tight, and with flange larger than opening 105 may prevent the first catheter 107 from pulling back through opening 105 in the second shell 109. Similarly the second shell 109 may be attached to the distal end of the second catheter 108, for example by brazing, welding (including laser), adhesive or other bonding means.

The first shell 103 and the second shell 109 may be formed as hollow semi-spherical surfaces, which may, for example, have a circumference approximately that of half of a sphere. However, their longitudinal axis may either be longer or shorter than that of a true circle and the circumference may be more or less than a half of a true circle. The first and second shells 103, 109 may be fabricated, for example, from biocompatible materials such as NITINOL nickel titanium alloy, carbon fiber, polyester, or stainless steel.

The first shell 103 may be slightly smaller in nominal diameter than the second shell 109, and may be located within the confines of the second shell 109. The outer surface of the first shell 103 may substantially conform in curvature to that of the second shell 109 so as to permit the first shell 103 to rotate about its longitudinal axis with respect to the second shell 109. In some implementation, the first shell 103 and the second shell 109 may be slideable upon their outer and inner respective surfaces, which also may be in contact. In a preferred embodiment, the first and second shells 103, 109 each have a circumference approximately that of half a circle (i.e., 180 degrees), although other configuration may also be used.

In one embodiment, the operator may be provided with a kit that includes various sizes of each of shells 103, 109. Preferably, the kit includes a plurality of interchangeable shells 103, 109, which the operator may select a combination of shells 103, 109, for example, based on the size and/or shape of the arteriotomy or other percutaneous procedure to be performed. Additionally, the kit may include printed instructions, and additional components, that may be suitable for therapeutic, pre-treatments, and/or other post-manufacturing procedures.

Figure 1C:
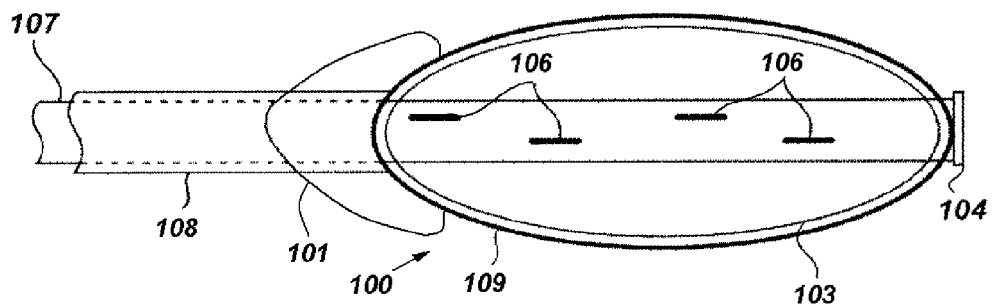
FIG. 1C is a top view of the lateral incision catheter shown in FIG. 1A.

FIG. 1C shows a top view of the lateral incision catheter 100 shown in FIG. 1A. One or more vacuum openings 106 are shown near the distal end of the inner catheter 107. The proximal end of the inner catheter 107 may be connected to a vacuum supply (not shown). The vacuum openings 106 may be used to draw the dual lumen lateral excision catheter device 100 toward a target site, like pulling drumhead and drum together. A fitting (not shown) may be provided on the proximate end of the first rotating catheter 107 for attachment to a vacuum source. In addition, the vacuum openings 106 may be used to remove bodily liquids, such as blood, from the vicinity of the distal end of the lateral incision catheter 100. As noted, excised tissue may be retained by the lateral incision catheter 100 for removal from the body through a hemostatic guiding catheter 5.

Figure 1D:
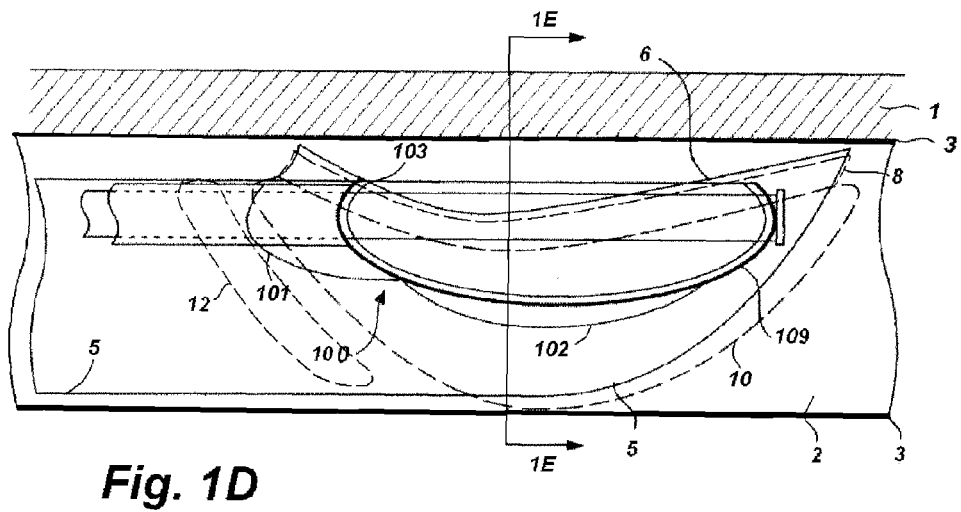
FIG. 1D is side view of the lateral incision catheter shown in FIG. 1A positioned in an hemostatic guiding catheter within a lumen of the body.

FIG. 1D shows the dual lumen lateral incision catheter 100 located inside a hemostatic guiding catheter 5 that is placed inside the artery 2 surrounded by tissue 1 that is adventitial to artery 2. It will be noted that certain features of the lateral incision catheter 100, would not ordinarily be visible from this vantage point (for example, being hidden by the hemostatis guiding catheter 5). However, as mentioned above, they are drawn in ordinary form (rather than in ghost line).

The dual lumen lateral incision shell catheter device 100 may be advanced through the hemostatic guiding catheter 5 to a pre-selected arteriotomy site. The hemostatic guiding catheter 5 may be formed of biocompatible materials, such as polymer, nylon, or other flexible metal. In one implementation, a hypotube, for example, manufactured by Creganna, Inc. may be used. Thus, when a hemostatic catheter is used it may be advanced percutaneously to a target site. Once there, a practitioner may guide the lateral incision catheter, within the hemostatic catheter, to the target site. Once at the target site, a lateral incision may be made by the lateral incision shell catheter 100, through the wall, in which the catheter resides and into the tissue or other material surrounding the target lumen wall.

The lateral incision shell catheter 100 may be used, for example, to produce an arteriotomy in a peripheral artery. The hemostatic guiding catheter 5 may be located within the artery 2 proximate to the tissue 1 to produce hemostasis at that target site before making the arteriotomy. Preferably, the lateral incision catheter 100 may be attached by inflated balloon 101 and balloon 102 to an inner surface of the hemostatic guiding catheter 5, so that the operator positions the lateral incision catheter 100 proximate to the target site by locating the hemostatic guiding catheter 5 thereto.

In addition, the lateral incision shell catheter 100 may be advanced independently through the hemostatic guiding catheter 5, after the hemostatic guiding catheter 5 has been properly positioned or established hemostasis at the target site. In one embodiment, one or more annular balloons 8, 10 and 12 may be placed around hemostatic guiding catheter 5 to establish hemostasis or otherwise form a seal at target area in the artery 2 (or other vessel) and thus, prohibiting the flow of blood or other fluids to the target site. In addition, the balloons 8, 10 and 12 help support and guide the catheter 5 within the artery 2. In other implementations, the lateral incision shell catheter 100 may be located proximate to the target site, without the use of a hemostatic guiding catheter 5

Figure 1E:
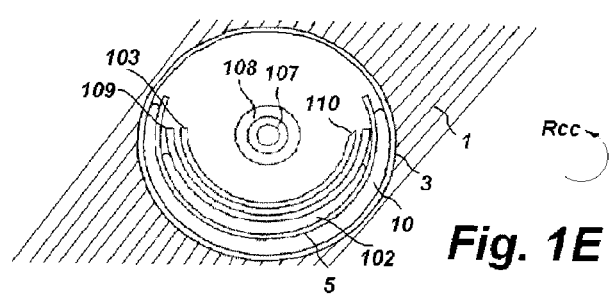
FIG. 1E is a cross-sectional view taken along line 1E-1E in FIG. 1D.

After the hemostatic guiding catheter 5 has established hemostasis at this site, the lateral incision shell catheter 100 may be advanced laterally to artery wall 3 through a distal opening 6 in the hemostatic guiding catheter 5. In some implementations, the opening 6 of the hemostatis guiding catheter 5 may have a "saddle" shape so as to be contiguous with the artery wall 3. This saddle-shape may more efficiently form a seal with the artery wall 3. The lateral incision shell catheter 100 may then be used to excise tissue from artery wall 3 to form an arteriotomy. Other uses are also possible FIG. 1E shows a cross-sectional view of the lateral incision catheter 100 taken along line 1E-1E of FIG. 1D. As can be seen, by rotating the first shell 103, via the rotating inner catheter 107, the first shell 103 may rotate in the direction $R_{CC}$ and, thus, out of the confines of the second shell 109. As such, the cutting surface of the first shell 103 may be exposed to the artery wall 3 to perform cutting.

Figure 1F:
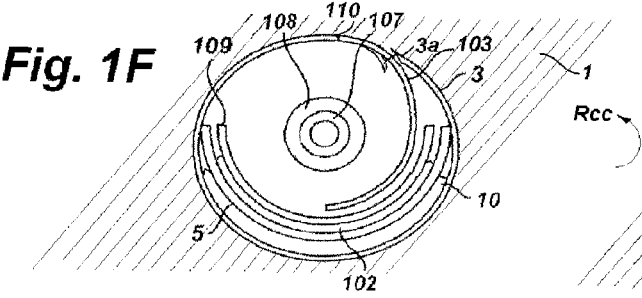
FIG. 1F is a sectional view of the distal end of a lateral incision catheter during a procedure.

FIG. 1F shows the same view shown in FIG. 1E where the first shell 103 has been further rotated in the direction $R_{CC}$ and the cutting surface 110 has begun cutting the artery wall 3a. Rotation of the first shell 103 exposes the cutting surface 110 to the artery wall 3, which pierces the surface thereof. The artery wall 3a may bow slightly during cutting.

Figure 1G:
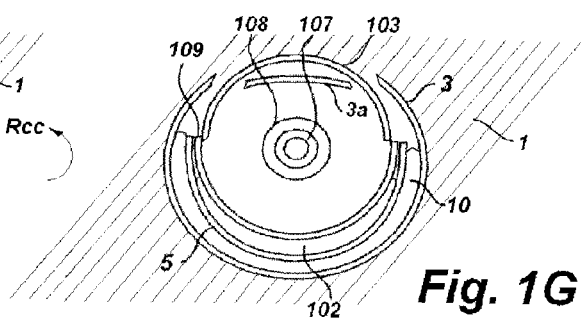
FIG. 1G is a sectional view of the distal end of a lateral incision catheter during a procedure.

FIG. 1G shows the same view shown in FIG. 1E after the cutting of the artery wall 3 has been completed. An excised portion 3b of artery wall 3 has been removed from the artery and is located in the second shell 109.

In one implementation, the operator may position the first shell 103 approximately 180 degrees from the second shell 109. As such, the first shell 103 and the second shell 109 may form a substantially closed container for removing the excised tissue 44 from the body. Sealing member (such as gaskets) may be provided, for example, at the interface of the first shell 103 and the second shell 109 to form a hermetic seal when the container is closed.

Figure 2A:
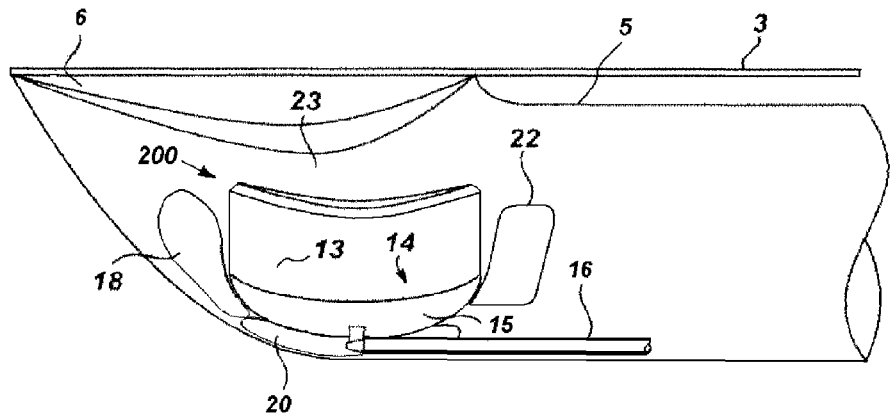
FIG. 2A shows a lateral incision catheter inside a guiding catheter, according to embodiments of the invention, wherein a cutting surface is in a retracted position.

FIG. 2A shows a lateral incision cup catheter 200, according to a second embodiment of the invention. The lateral incision catheter in FIG. 2A includes an incision cup 14 having a mouth 23, a bottom portion 15 and a generally cylindrical side wall 13.

The incision cup 14 may have a circular or oval shape such that it can fit within the opening 6 of the hemostatis guiding catheter 5. The opening 6 of the hemostatis guiding catheter 5 may have a saddle-shape so as to be contiguous with the artery wall 3 to more efficiently form a seal with the artery wall 3. The incision cup 14 made be integrally formed from a biocompatible material such as, NITINOL nickel titanium alloy, stainless steel or a hard polymer.

The incision cup 14 is shown located in hemostatic guiding catheter 5 with its open mouth portion 23 facing the distal opening 6. The lateral incision cup catheter 200 may be advanced to artery 2 in a similar manner as used to position the lateral incision catheter 100, within the artery 2. The incision cup 14 may be advanced within the hemostatic guiding catheter 5 by a supply catheter 16, which may be attached to any part of incision cup 14, including an attachment point at its bottom (as shown).

In one embodiment, a cutting surface 26 may be located on the edge of the open mouth portion 23 generally parallel to the longitudinal axis of incision cup 14 of supply catheter 16.

One or more push balloons (represented by the outlines of three partially inflated push balloons) may be attached to incision cup 14. In one implementation, three push balloons are provide including a distal push balloon 18, a middle push balloon 20, and a proximal push balloon 22. The distal push balloon 18 and the proximal push balloon 22 extend toward the open mouth 23 of the incision cup 14 and are attached near the bottom portion 15 of incision cup 14 so as to maintain contact with the sides of the hemostatic guiding catheter 5 when inflated. The middle push balloon 20 may provide the majority of the force for pushing the incision cup 14 toward the distal opening 6 and thus, the artery wall 3 to accomplish an arteriotomy. The balloons 18, 20, 22 may be made of biocompatible materials such as, for example, polyurethane, nylon elastomers or other thermoplastic elastomers. A plurality of fluid supply lines (not shown) may be carried inside or attached to the outside of supply catheter 16 for inflating the balloons.

Before the cutting surface 26 on the diameter of incision cup 14 may be used to cut an arteriotomy, hemostasis should be established by hemostatic guiding catheter 5, so that blood does not escape from artery 2 through the arteriotomy. In one implementation, the incision cup 14 may have a saddle shape so as to be substantially contiguous with artery wall 3. Moreover, the incision cup 14 may be connected to a source of vacuum (not shown) to apply a vacuum to artery wall 3 to pull the artery wall 3 toward the diameter cutting blade 26.

Figure 2B:
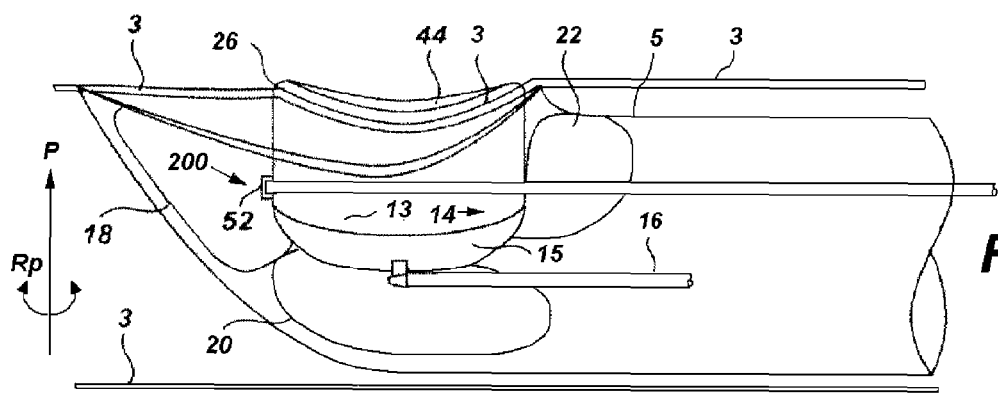
FIG. 2B shows the lateral incision catheter shown in FIG. 2A, where the cutting surface is partially extended outside a guiding catheter, by balloons in a partially inflated state.

FIG. 2B shows the lateral incision cup catheter 200 shown in FIG. 2A where one or more push balloons are partially inflated moving the cup toward the exposed artery wall. Inflation of the push balloons 18, 20, 22 cause the incision cup 14 to rise in a direction P and stabilize with respect to the walls of hemostatic guiding catheter 5.

In one implementation, the cutting surface 26 may have a sharp edge and even a serrated cutting edge. In some implementations, the connection between incision cup 14 and supply catheter 16 may be at the bottom portion 15 of incision cup 14 and a bearing 17 may be placed at their connection point, which allows the incision cup 14 to rotate in a direction $R_P$ relative to the supply catheter 16. In use, the incision cup 14 may be advanced in the direction P and rotated back-and-forth in the direction $R_P$ to create a sawing motion. In other implementations, the cutting surface 26 may also be coated with a lubricious material as an aid in cutting through tissue.

A vacuum may be provided, through supply catheter 16, to the inside of the incision cup 14 and may hold material excised from the target site in incision cup 14 during its removal.

Figure 2C:
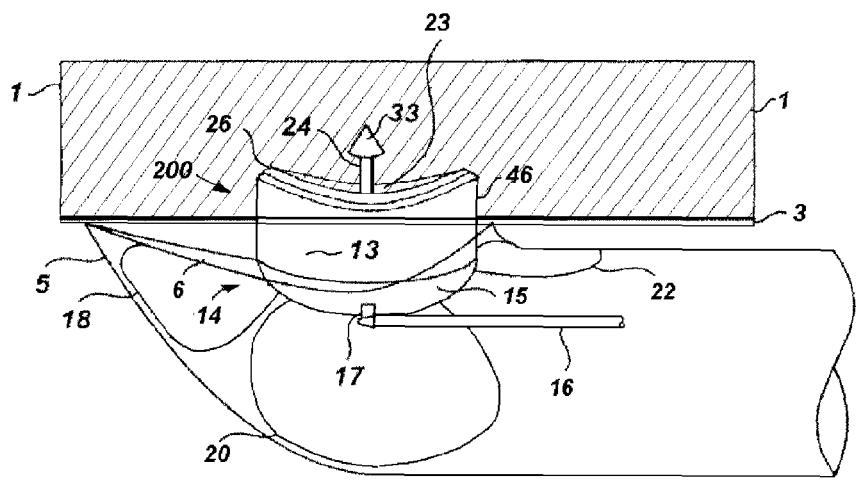
FIG. 2C shows the lateral incision catheter of FIG. 2A with the cutting surface extending into a target site and the balloons in an inflated state.

FIG. 2C shows push balloons 18, 20 and 22 fully inflated and incision cup 14 raised into the surrounding tissue 1 on the adventitial side of artery wall 3. A portion of the surrounding tissue 1 is shown as hatched in cross-section. The incision cup 14 is shown to have cut a cylinder of tissue, but the excised cylinder of cut tissue 1 is still attached to surrounding tissue at its top surface.

Figure 2D:
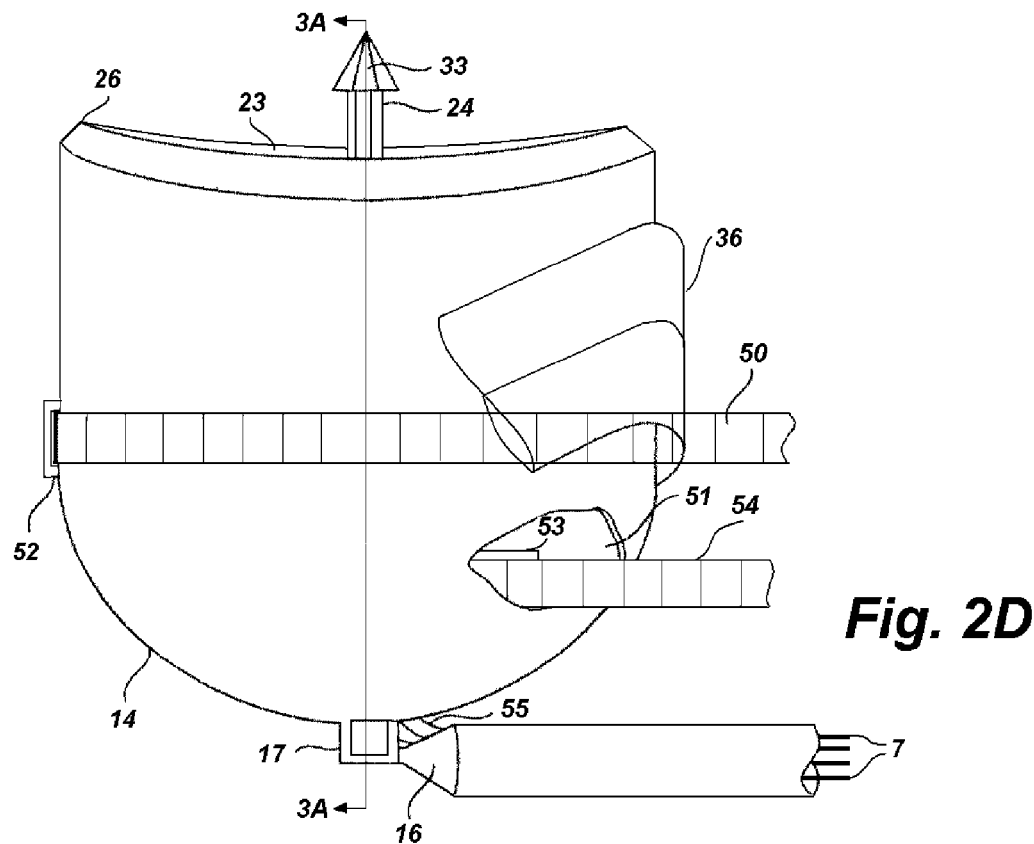
FIG. 2D shows an enlarged side view of an incision cup as may be used in the lateral incision catheter of FIG. 2A.

FIG. 2D shows an enlarged view of the incision cup 14. As can be seen, a cup strap 50 may be positioned around the circumference of the incision cup 14 to rotate the incision cup 14. The cup strap 50 extends proximally through the hemostatic guiding catheter 5 to a location beyond the proximal end of hemostatic guiding catheter 5 where it is used by the operator (surgeon) to alternately pull one side and then the other in a sawing motion to assist in cutting tissue with sharp edge 26. A hangar 52 located on the sidewall of the incision cup 14 may help to maintain the cup strap 50 in place when it's slack. Supply lines 7 are also visible exiting the catheter 16. These supply lines control the inflation and deflation of the balloons on the outside of the cup, Nos. 18, 20 and 22.

Fluid supply lines 7 may be provided in the supply catheter 16 for inflating the various push balloons. In addition, a lateral incision balloon 36 may be attached to the outer surface of the sidewall 13 of cup 14. In one implementation, attachment may include an adhesive or glue. The lateral incision balloon 36 is shown in a partial view and deflated in FIG. 2D, and will be discussed in further detail with regard to the embodiment shown in FIGS. 4A-4D (below).

Figure 2E:
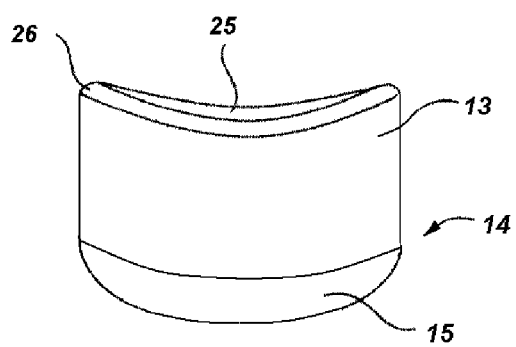
FIGS. 2E and 2F show constructions of the incision cup of the lateral incision catheter of FIG. 2A.
Figure 2F:
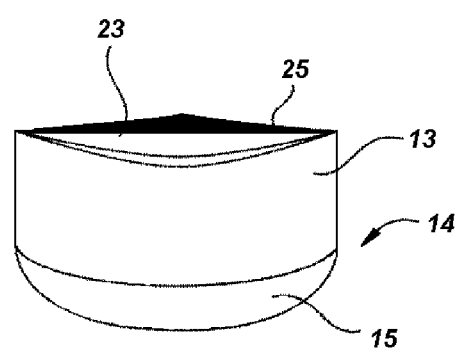

FIGS. 2E and 2F show constructions for the cup 14. For example, as shown in FIG. 2E the cup 14 may have a saddle shape mouth portion 23 so as to be more contiguous with the artery wall 3. The edge of the mouth portion 23 may include the edge cutting surface 26. In FIG. 2F, the cup 14 may further be provided with a cutting blade 25 placed across the diameter of the saddle shaped mouth portion 23.

FIG. 3A shows a cross-section of the cup 14 taken along line 3A-3A in FIG. 2D. The cup 14 generally includes the mouth portion 23, the cylindrical wall 13 forming an upper section, and an lower section 15 separated by an internal partition 11 that serves as a partition between the upper section 13 and the lower section 15. The upper and lower sections 13, 15 may be formed of a biocompatible material, such as stainless steel or other metal and/or hard plastic, and integrally joined together for example, by adhesive, brazing, electrical welding, laser, or other appropriate joining means. The rotation shaft 24 passes through a shaft opening 19 in the partition 11 to another shaft opening 19 in the bottom of the lower section 15 of the incision cup and rises above the plane of the cutting edge 26. A bearing (not shown) may be provided at openings 19, to support the rotation shaft 24. A flanged point 33 may be located at the distal end of the rotation shaft 24 and may be used to penetrate the tissue 1 above the level of cutting edge 26.

The rotation shaft 24 includes at least one arm 32 with a sharp leading edge, where the arm 32 extends radially from the rotation shaft 24 and includes an end piece 35 which engages a helical groove 28 located in the inner cylindrical surface of the cup 14. A pair of opposed arms 32 may be provided at approximately 180 degrees apart. At the distal ends of each of the arms 32, end pieces 35 on the pair of cutting blades 32 fit into helical grooves 28 and/or the circular groove 30 located on the inner surface of the upper section 13.

In some implementations, groove 28 may be double helix grooves to accommodate the pair of arms 32. Both groove 28 and the circular groove 30 may be cut, etched or otherwise provided in the inside cylindrical surface of the upper section 13. In other implementations, the groove 28 and circular groove 30 may formed as a liner or separate element that is joined to the inner surface of the cylindrical wall 13, for example, by welding, brazing, or an adhesive.

The arms 32 may be radially attached to a connecting ring 34 that fits around rotation shaft 24. The open center of connecting ring 34 has substantially the same cross-sectional shape as, and slidably fits over, the rotation shaft 24. As such, the connecting ring 34 engages with the rotation shaft 24 to permit axial motion therebetween only. In some implementations, this may be a keyed or splined connection to limit rotation of the connecting ring 34 with respect to the shaft 24. Thus, rotation of the shaft 24 may be provide a corresponding rotation motion in the connecting ring 34, while the grooves 28, 30 provide an axial motion.

Rotational force may be transmitted from rotation shaft 24 to the connecting ring 34 and to the pair of arms 32, while the connecting ring 34 and cutting blades 32 are free to move up rotation shaft 24 along the grooves 28. The rotation shaft 24 passes through shaft opening 19 in wall 11.

One or more bearings 17 may be provided to rotationally support the of the rotation shaft 24. In one implementation, a rotation wheel 53 may be attached to the bottom portion of the rotation shaft 24. The surface of rotation wheel 53 is configured for engaging a wheel strap 54 for effecting rotation of the rotation wheel 53 that may be pulled by the operator to effect rotation of the shaft 24.

The geometry of the wheel 53 and double helix groove 28 can determine the cutting motion. For example, one half of one rotation of the rotation wheel 53 causes the cutting blades 32 to move up the groove 28 and into circular groove 30. A further half-rotation of the wheel 53 may then complete the sweep of circular groove 30 by pair of cutting blades 32.

The bottom of flanged point 33 provides a lip that prevents the connecting ring 34 from moving higher and thus, prevents cutting blades 32 from rising above the upper edge of upper section 13. When one rotation of the rotation wheel 53 is completed, the top of the cylinder of tissue 1 in incision cup 14 will be cut free from surrounding tissue 1 for removal from the body. The pair of cutting blades 32 may hold the tissue in incision cup 14 as it is withdrawn.

FIG. 3B shows an implementation for rotation of the shaft 24. A toothed wheel or gear 57 having teeth around the outer edge may be used instead of wheel strap 54 for rotating rotation wheel 53. In this embodiment, an electrical motor 58 engages the toothed wheel 57. Rotation of the motor 58 may be controlled by the operator, for example, by selectively controlling electricity to the motor 58 via electrical wires 59.

Figure 3C:
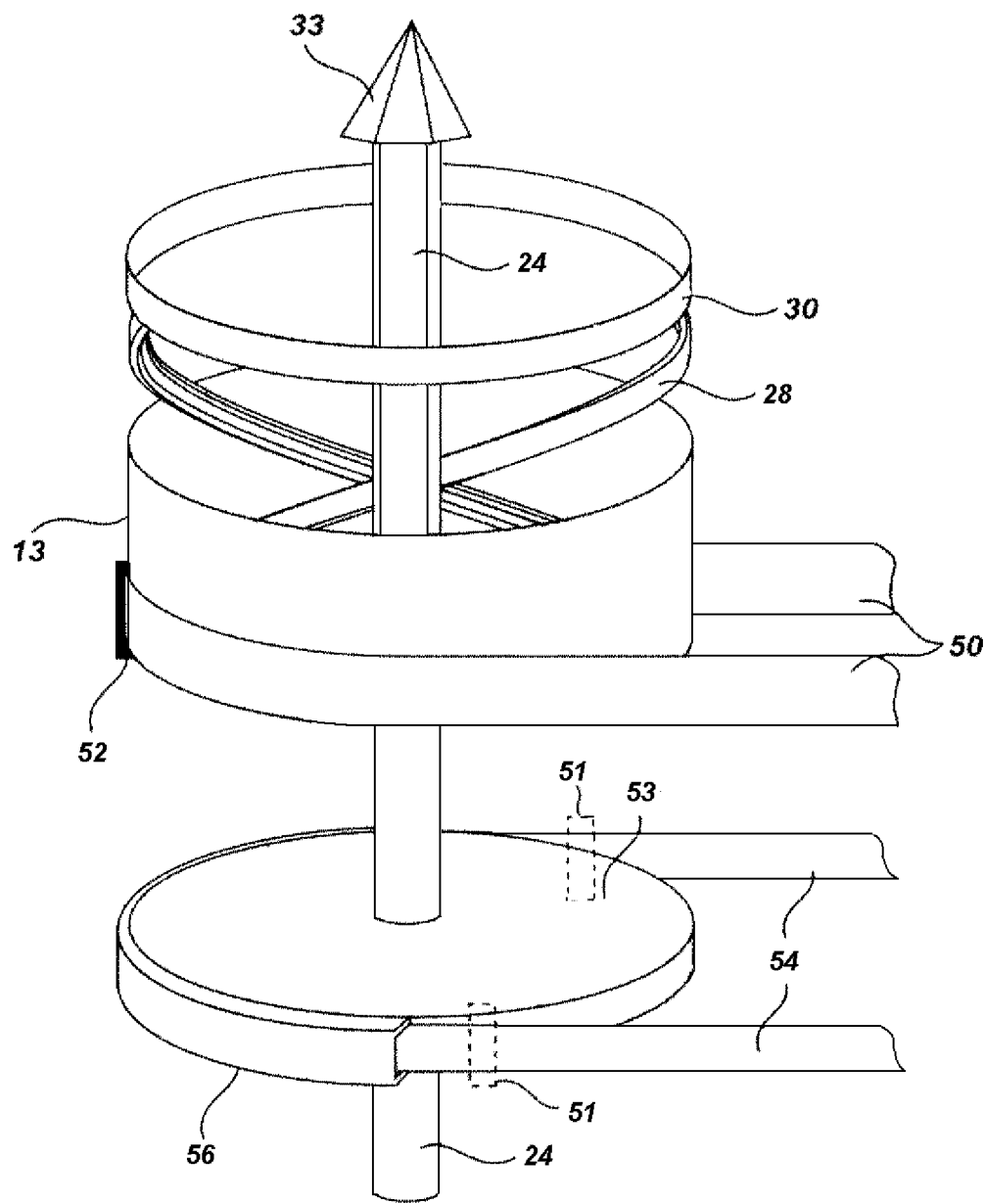
FIG. 3C shows a perspective view of the cutting elements within the incision cup shown in FIG. 3A.

FIG. 3C shows a perspective view of the incision cup 14 shown in FIG. 3A. For ease of illustration, most of the surface of incision cup 14 has been omitted from the figure. In some implementations, a holding rim 56 may be attached to the inside wall of the incision cup 14 wall so as to extend on both sides of rotation wheel 53 to help keep the wheel strap 54 in place around about half of the circumference of rotation wheel 53. The wheel strap 54 is shown coming through side openings 51 in lower section 15 and going around rotation wheel 53. The wheel strap 54 extends to the operator who pulls one side to turn rotation wheel 53.

In some implementations, the surface of rotation wheel 53 and/or the inner surface of wheel strap 54 may be coated with a sticky substance to increase traction. The pulling wheel strap 54 rotates the rotational shaft 24 that turns the pair of cutting blades 32 in the double helix groove 28 and circular groove 30 to cut the top of the tissue located in incision cup 14.

Figure 4A:
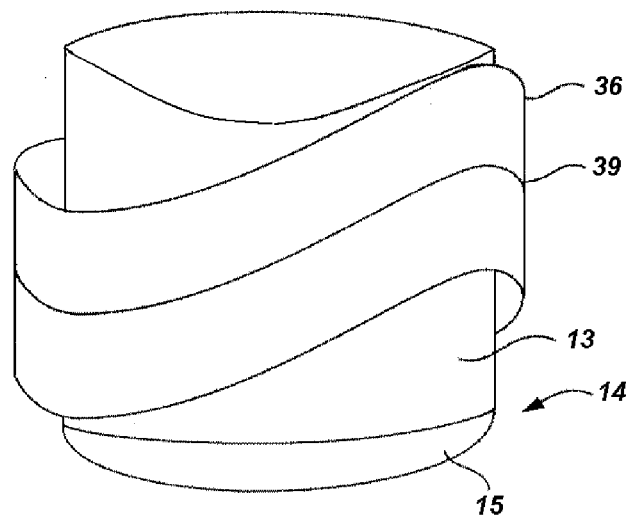
FIG. 4A shows an outside surface of an incision cup and an incision balloon in accord with embodiments of the invention.

FIG. 4A shows the outside of incision cup 14 and an incision balloon 36, according to a third embodiment of the invention. The incision balloon 36 may be used to make an incision in surround tissue 1 to excise a cylindrical space 48 (see FIG. 5C) in the surrounding tissue 1. In one implementation, the incision balloon 36 may be saddle-shaped to cut incision disc 44 to be substantially parallel to artery wall 3. The medial line curving through the uninflated balloon is a fold 39. In some implementation, the fold 39 may be a V-shaped.

Figure 4B:
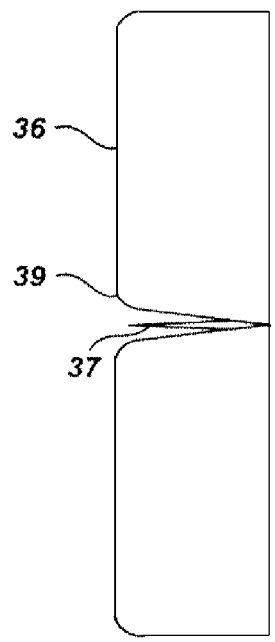
FIG. 4B shows an enlarged side view of the uninflated incision balloon of FIG. 4A.

FIG. 4B shows a cross-sectional view of the uninflated incision balloon 36 with incision blade segment 37 visible in the V-shaped fold 39. When inflated, incision balloon 36 pushes the apex of V-shaped fold 39 forward exposing incision blade segments 37 around the periphery of incision balloon 36 to perform cutting. The inflation balloon 36 may include a plurality of segments and an incision blade 37 may be provided in each inflation balloon segment 36 (not shown).

Figure 4C:
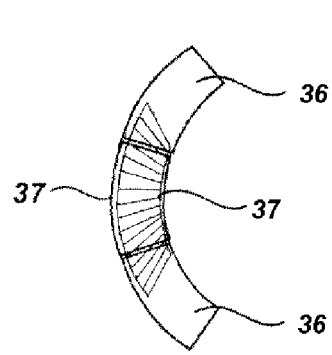
FIG. 4C shows a top view of the incision blades and the incision balloon of FIG. 4B.

FIG. 4C shows a top plan view of an incision balloon 36 and incision blades 37. When the incision balloon 36 is uninflated, the incision blades 37 generally overlap each other on the outer circumference of incision balloon 36. As the incision balloon is inflated, the incision blade segments 37 generally move out of the V-shaped fold 39. In one implementation, when incision balloon 36 is fully inflated its circumference may be about twice its uninflated circumference such that the incision blade segments 37 may be protruding from the outer circumference of the incision balloon 36.

Figure 4D:
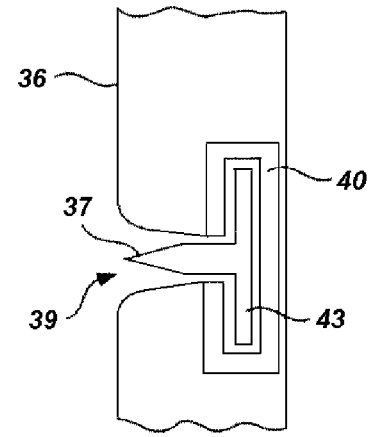
FIG. 4D is a detailed enlarged view of an embodiment of the V-shaped fold of FIG. 4A.

FIG. 4D is a detailed view of the V-shaped fold 39 showing the incision blade segments 37. The incision balloon 36 stretches as it is inflated while the incision blade segments 37 remain the same size. Thus, the incision balloon 36 retains the incision blade segments 37 while changing size is shown in this cross-section view. The base 43 of each incision blade 37 may be generally T-shaped and may be located in a C-shaped reinforcement extrusion 40 or groove at the apex of V-shaped fold 39. In the uninflated state, the reinforcement extrusion 40 is about the same circumference as the total of the incision blade bases 43. With inflation of the incision balloon 36, the reinforcement extrusion 40 becomes longer and slides over the incision blade bases 43 while effectively clamping them in place. This reinforcement extrusion 40 also reinforces incision balloon 36 at the apex of V-shaped fold 39 where back pressure from incision blade segments 37 cutting through tissue is generally focused. Thus, back pressure is distributed substantially uniformly over reinforcement extrusion 40. While the extrusion 40 is shown having as being generally C-shaped (rectangular) in cross section, it will be appreciated that the extrusion 40 could also be circular or other shapes so long this it keeps the incision blade base 43 clamped firmly in place while distributing back pressure.

Figure 5A:
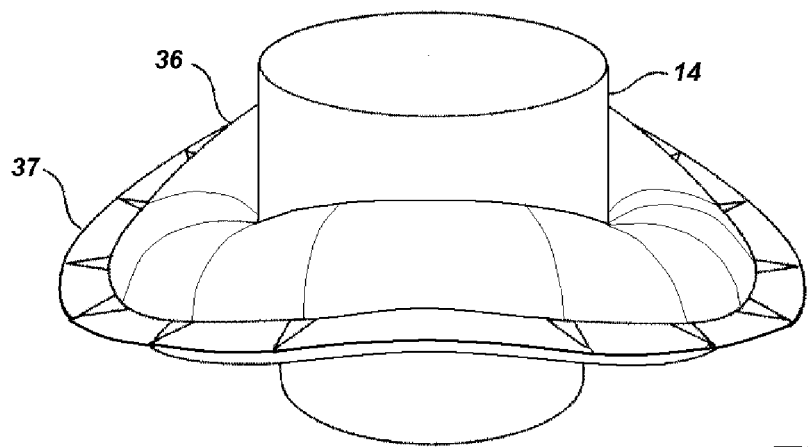
FIG. 5A shows on incision balloon of a lateral incision catheter in an inflated position with the incision blades extended substantially radially from the cup in accord with embodiments of the invention.

FIG. 5A shows the incision balloon 36 fully inflated with the incision blades 37 fully extended radially from the cup 14. This produces a saddle-shaped incision disc 44 outside an excised cylinder 48 of excised tissue.

Figure 5B:
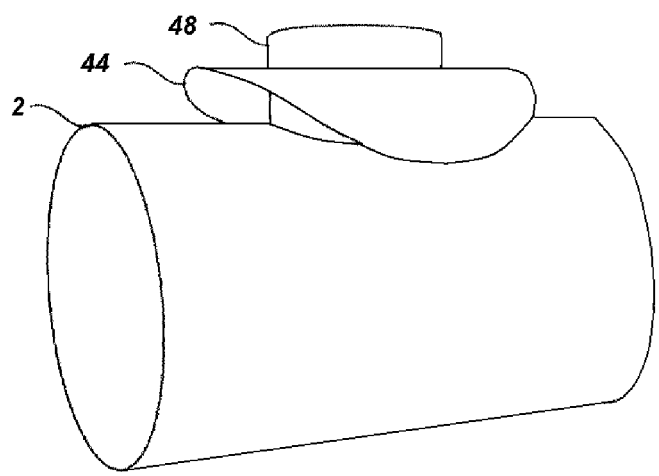
FIG. 5B shows a vessel having a lateral incision with an expanded balloon extending from the incision in accord with embodiments of the invention.

FIG. 5B shows the artery 2, the excised cylinder space 48 and the incision disk 44. These spaces were produced by the incision cup 14 when the tissue was removed. These figures shows the space created by excising and incising surrounding tissue 1. Incision disc 44 is substantially parallel to the wall of the artery 2.

Figure 5C:
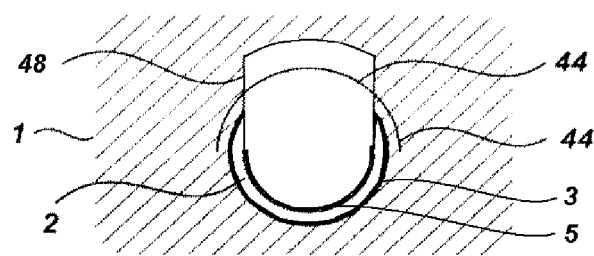
FIG. 5C shows a cross-sectional view of a lateral incision catheter at a target site.

FIG. 5C shows a cross-sectional view of artery 2 including the excision cylinder space 48 and incision disc 44 in tissue 1.

The excised portion 3b of the artery wall 3, which had previously been removed, is also shown.

Once the incision disc 44 has been used and removed, the physician may decide that this arteriotomy is sufficient and proceed with other steps involved in placing a bypass graft that make use of the hemostatic guiding catheter.

A physician may decide, for one of several reasons, that a certain additional treatment of the arteriotomy is needed. This might be indicated if excision disc 44 will not come free of surrounding tissue 1 for removal. Or it could be that the physician has reason to want hemostatic guiding catheter 5 attached to artery wall 3 and tissue adventitial to artery wall 3 to be removed to accomplishing this object.

FIGS. 6-12 show a method for forming a hemostatic clamp around the arteriotomy made by the lateral excision/incision device, according to embodiments of the invention.

Figure 6:
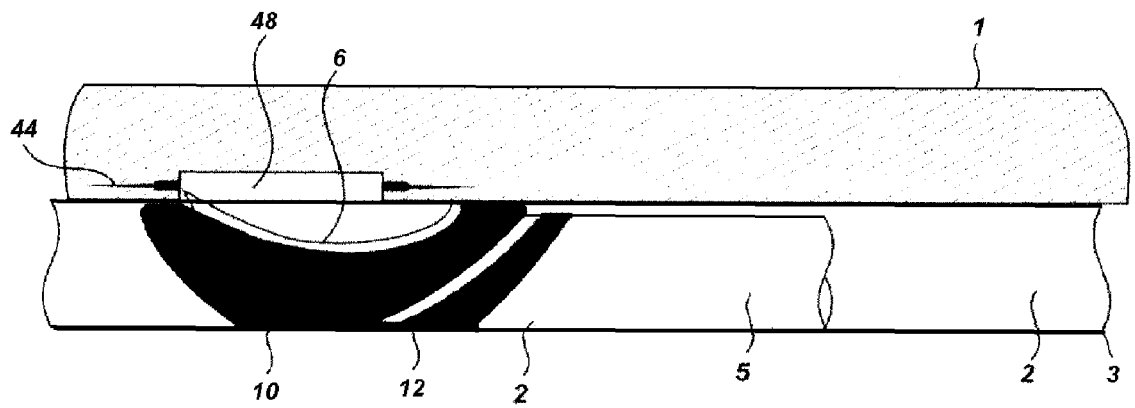
FIG. 6 shows a side view of a lateral incision catheter at a target site with incision blades from the catheter extended into the target site, in accord with embodiments of the invention.

FIG. 6 shows a cross-sectional view of the exterior of the hemostatic guiding catheter 5 with visible annular balloons 10, 12 and target tissue 1 (annular balloon 8 may also be used here and is not shown for ease of illustration.). The object of making incisions and excisions in tissue 1 adventitial to artery 2 is for placing the hemostatic guiding catheter 5 in the excised/incised space should the physician decide to attach the hemostatic guiding catheter 5 to artery wall 3. The annular balloon 10 is shown inflated so as to make contact with the wall of artery 2 all around the circumference of the incised/excised arteriotomy. In some implementations, this produces hemostasis while excisions/incisions were made. If hemostatic annular balloons are desired on the adventitial side of the artery, the hemostatic guiding catheter 5 is pushed into the space of cylinder section 15 and incision disc 44 on-against the adventitial side of the artery 2. For example, the distal end of hemostatic guiding catheter 5 is raised or pushed against the artery wall 3.

Figure 7:
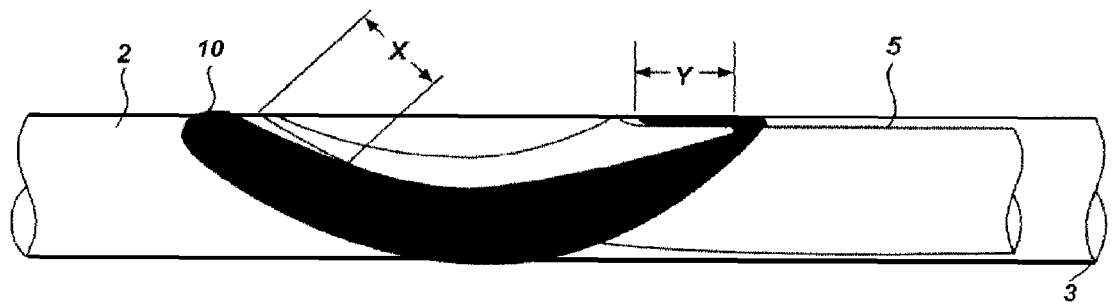
FIG. 7 shows a side view of a lateral incision catheter within a vessel of a patient, in accord with embodiments of the invention.

FIG. 7 shows a further view of inflated annular balloon 10 on the hemostatic guiding catheter 5 in the artery 2. The annular balloon 10 will move as the distal end of hemostatic guiding catheter 5 is pushed and lifted through the arteriotomy and into excised cylinder 15 by a combination of forces, including a force vector from the balloon 10 pushing up on hemostatic guiding catheter 5 and a force vector parallel to the longitudinal axis of hemostatic guiding catheter 5 being delivered by an operator pushing the hemostatic guiding catheter 5. These two force vectors will cause the distal end of hemostatic guiding catheter 5 to rise through the arteriotomy for the distance marked "X" and to go forward for the distance marked "Y." As this takes place, the annular balloon 10 is pushed back. This action pushes more fluid in annular balloon 10 under the hemostatic guiding catheter 5 thus producing more upward force vector push. The effect is to raise the distal end of hemostatic guiding catheter 5 into the excised cylinder 48, pushing adventitial tissue out of the way as it moves.

Figure 8:
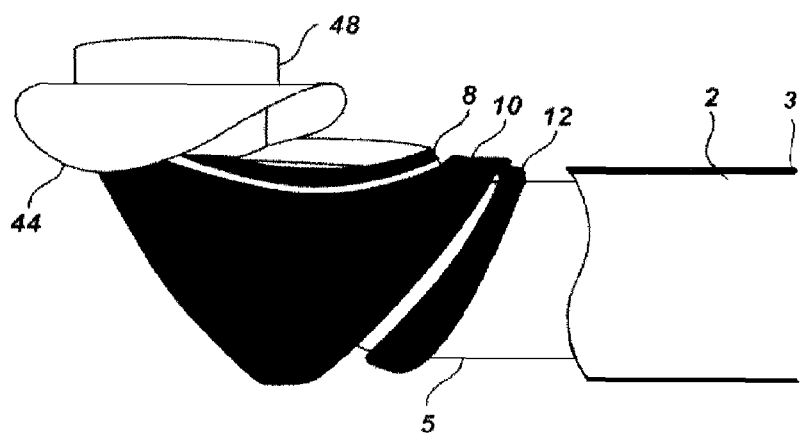
FIG. 8 shows a side view of the distal end of a three balloon lateral incision catheter with incision blades and an incision cup extending outside of a catheter, in accord with embodiments of the invention.

FIG. 8 shows a 3-dimensional view of the hemostatic guiding catheter 5 entering the excised cylinder section 48 proximate to the incised disc 44. The wall of the artery 2 has been partially omitted from FIGS. 8-11 for clarity, so that the hemostatic guiding catheter 5 can be seen going through the arteriotomy and into the excised cylinder 48. As annular balloon 10 is pushed back, the annular balloon 8 is exposed, as is seen around the distal end of the hemostatic guiding catheter 5.

Continued pushing of the hemostatic guiding catheter pushes it up into excised cylinder 48. At this instance, the balloon 12 has not been inflated and is shown in outline. When the hemostatic guiding catheter 5 is also being pushed forward by the operator, it also causes it to push against the wall of excised cylinder 48 distorting its shape as well as the shape of incision disc 44.

Figure 9:
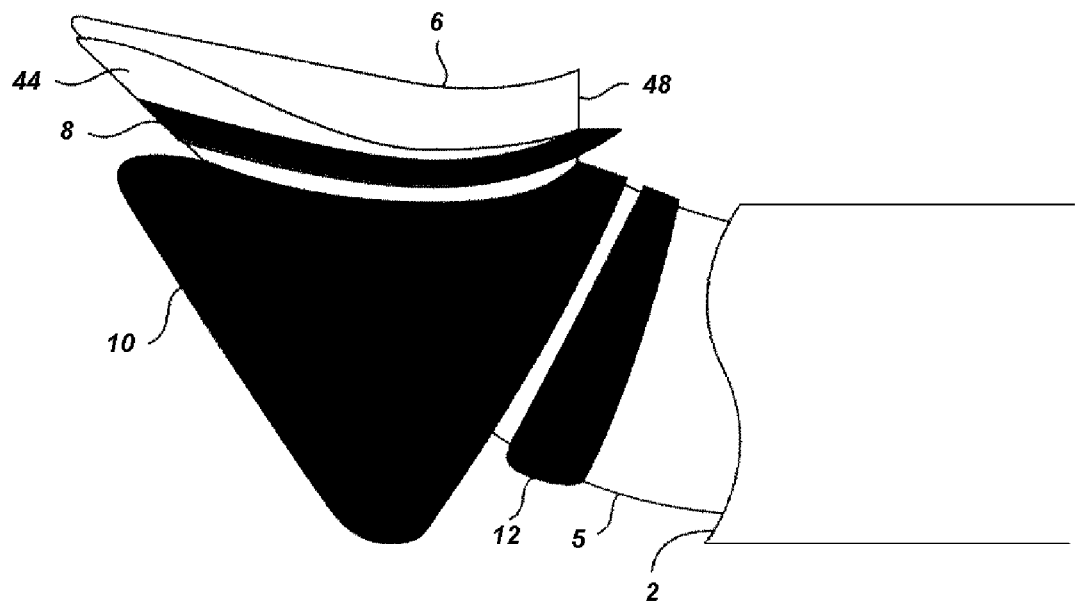
FIG. 9 shows a side view of the distal end of a three balloon lateral incision catheter with incision blades and an incision cup extending outside of a catheter, in accord with embodiments of the invention.

FIG. 9 shows the hemostatic guiding catheter 5 being further pushed and raised to distort the excised cylinder 48 by forcing its way in. This pushing is continued until the proximal side of the hemostatic guiding catheter 5 is in line with the excised cylinder 48.

Figure 10:
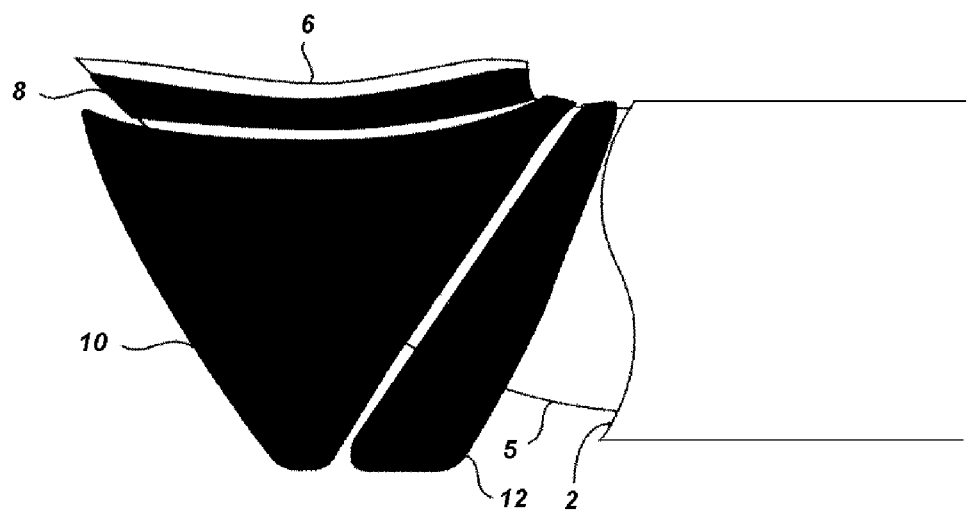
FIG. 10 shows a side view of the distal end of a three balloon lateral incision catheter with the three balloons in an inflated configuration, in accord with embodiments of the invention.

FIG. 10 shows the hemostatic guiding catheter 5 after it has been pushed into excised cylinder 48. This has distorted the original shape of the excised cylinder 48 to be closer to the shape of the hemostatic guiding catheter 5. The distal portion of the hemostatic guiding catheter 5 is still slightly higher than the portion of hemostatic guiding catheter 5 on the lumen side of distal opening 6. This may be corrected by inflating balloon 12 to exert more upward push (if necessary).

Figure 11:
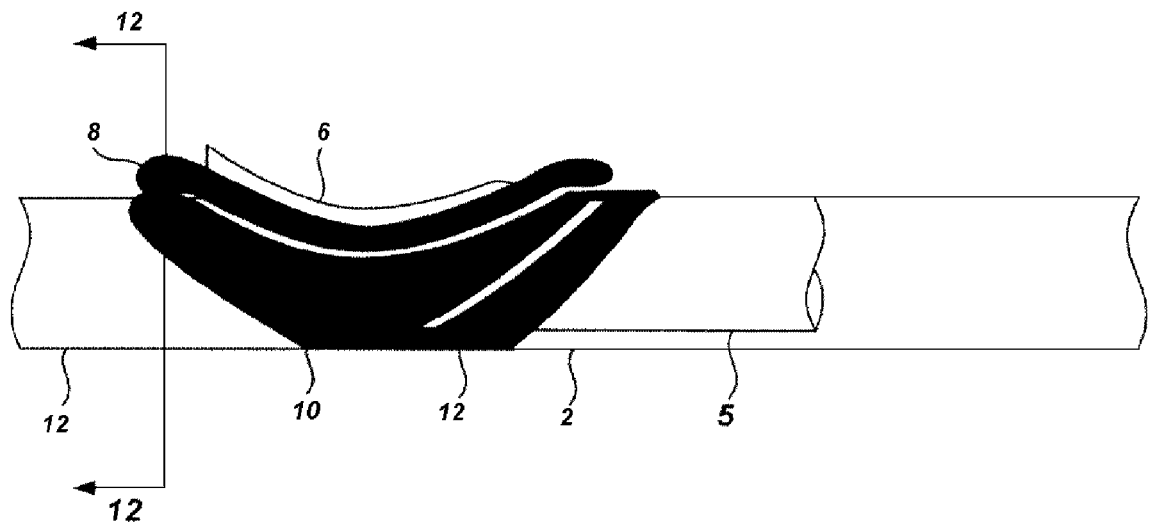
FIG. 11 shows a side view of the distal end of a three balloon lateral incision catheter at a target site with the balloons in an inflated configuration, in accord with embodiments of the invention.

FIG. 11 shows hemostatic guiding catheter 5 fully extended up into the excised cylinder 15 with the annular balloons 10 and 12 fully inflated and annular balloon 8 is uninflated. Hemostatic guiding catheter 5 has been leveled by the force from annular balloon 12 pushing up the more proximal part of distal opening 6 in hemostatic guiding catheter 5. Annular balloon 8 is now on the adventitial side of artery 2 and ready to be inflated.

Figure 12:
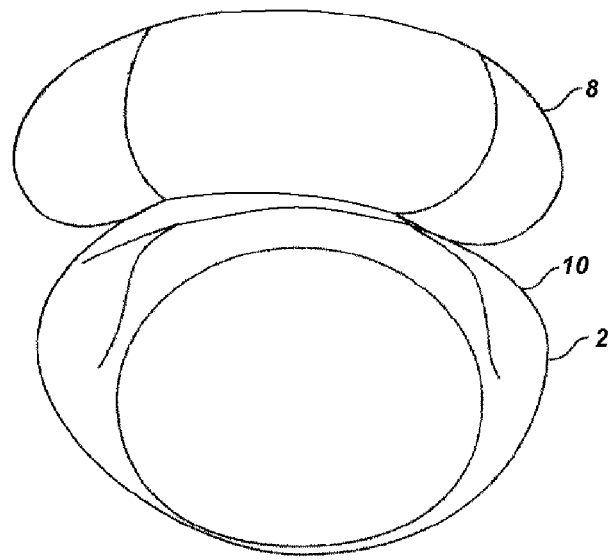
FIG. 12 shows a sectional view taken through sectional line 12-12 of FIG. 11, in accord with embodiments of the invention.

FIG. 12 shows a cross-sectional view of annular balloons 8, 10 and 12 fully inflated. This is the same state depicted in cross-sectional view shown in FIG. 11, but is shown with three-dimensional shapes The inflated annular balloon 8 is on the adventitial side of artery 2 fitting against annular balloon 10 located in the artery 2. The artery wall 3 is located in the white space between the balloons 8, 10 and surrounds the balloon 10 in a direction parallel the artery 2. The balloon 10 forms a barrier to blood passing through artery 2. The hemostatic guiding catheter 5 has been omitted from the figure for clarify, although its location is inside balloon 10 turning up approximately 45 degrees through a hole in the center of the balloon 8. The saddle shape of most distal annular balloon 8 and next most distal annular balloon 10 clamp the wall of artery 2 between them. The annular balloon 10 is seen to be narrow in the proximal area and of large circumference in the distal area where it extends outwardly from its circumference of attachment.

The "white line" or space between the annular balloons 8 and 10 is where the wall of artery 2 has been clamped between these two balloons. This clamping also attaches the hemostatic guiding catheter 5 to artery wall 3 and completes the hemostasis originally maintained by annular balloon 10. The hemostatic guiding catheter 5 is ready to guide additional elements to this site to complete the placement of a bypass graft.

The lateral incision shell catheter 100 and lateral incision cup catheter 200 may be introduced into the body through any natural orifice, as in a colonoscopy or prostatectomy, or though an opening made by a physician. Typically a physician will use the Seldinger technique to introduce catheter-based instruments into the body and this technique may be used with the catheter-based devices 100, 200 and 5. The technique involves using a syringe-like device to puncture the skin and enter the femoral at a location where the femoral artery is close to the skin, as in the groin. A sheath is placed over the syringe needle and the syringe is withdrawn. Thus, the sheath provides a path from outside the body to inside the femoral artery for introducing catheter-based instruments. Catheter-based or other instruments may be directed by an operator (physician) toward the heart or toward the lower limbs to be manipulated by the operator to perform various functions, including those revealed herein. The catheter based-devices cutting devices 100, 200 may be introduced in this way with or without the introduction of the hemostatic guiding catheter 5.

While embodiments have been described in connection with what is presently considered to be the most practical and preferred, it is to be understood that further modifications are possible. This application is intended to cover any variations, uses, equivalent arrangements or adaptations of the invention following, in general, the principles of the invention and including such departures from the present disclosure and followed in the spirit and scope of the appended claims.

Steps described for each process may be omitted or the order changed or performed simultaneously without deviating from the spirit or scope of the invention. It should be understood that a specific application situation involving a peripheral artery with an occlusion is used to represent the general case of a vessel of a patient's body.

What is claimed is:

1. A lateral incision catheter for incising adjacent tissue at a target site, comprising:
    a rotating first catheter of generally circular circumference, including a proximal end, a distal end and a lumen extending therebetween;
    a first shell formed as a hollow semi-spherical surface of a hard, rigid material with a circumference approximately that of half a true circle, such that the circumference extends approximately 180 degrees, the first shell extending in a longitudinal direction of the first rotating catheter; and the first shell having a cutting surface located on each side; wherein the first rotating catheter is bonded to the first shell near a distal end of the first rotating catheter;
    a rotating second catheter of generally circular circumference having a proximal end, a distal end and a lumen extending therebetween, being larger than, and surrounding said rotating first catheter;
    a second shell formed as a hollow semi-spherical surface of a hard, rigid material with a circumference approximately that of half a true circle, such that the circumference extends approximately 180 degrees, the second shell extending in a longitudinal direction of the rotating second catheter, the second shell having a cutting surface located on each side, the second shell being larger than the first shell so as to surround the first shell, the rotating second catheter is bonded to the second shell near a distal end of the rotating second catheter; wherein the rotating first catheter passes through an opening in the second shell; and wherein an outer surface of the first shell substantially conforms in curvature to that of the second shell to permit the first shell to rotate about its longitudinal axis with respect to the second shell;
    whereby the lateral incision catheter is configured to be advanced to a pre-selected site in the lumen of a blood vessel, wherein one or both of the rotating first catheter and rotating second catheter is configured to be rotated to properly position the first and second shells radially with respect to the pre-selected site, the rotating first catheter and rotating second catheter are then configured to rotate in opposite directions to allow the cutting surfaces of the first and second shell edges to engage the adjacent tissue to cut out and remove a section of a vessel lumen wall between the first and second shell edges, and;
    wherein after the first and the second shells have rotated about 180 degrees, a substantially closed container is formed by the first and second shells, and wherein the closed container holding the excised portion of vessel lumen wall is configured to be removed from the blood vessel by retraction of the lateral incision catheter.

2. The lateral incision catheter according to claim 1, further comprising with a first inflatable balloon attached to an outside surface of the second shell and a second inflatable balloon attached to the surface of the rotating second catheter and the outside surface of the second shell; whereby inflation of one or both balloons pushes the lateral incision catheter laterally away from the balloons to snugly secure the second shell edges against the lumen wall at the pre-selected site, thereby permitting the first shell to cut the adjacent tissue.

3. The lateral incision catheter according to claim 1, wherein the lateral incision catheter is configured to be advanced through a hemostatic guiding catheter located within an artery, the hemostatic guiding catheter positioned to form a seal at a target area around the pre-selected site to prohibit blood flow or other fluids to the site such that the lateral incision catheter can excise tissue from the artery wall to form an arteriotomy.

4. The catheter according to claim 1, further comprising: a rotating flange secured to the distal end of the rotating first catheter and extending radially outward from the circumference of the rotating first catheter, wherein the rotating flange prevents the rotating first catheter from pulling back through the opening in the second shell.

5. The catheter according to claim 1, further comprising: one or more vacuum openings provided in a distal portion of the rotating first catheter through which a vacuum from the proximal end of the rotating first catheter can be applied; whereby the vacuum draws the first and second shell edges of the lateral incision catheter toward the target site, thus snugly securing the second shell against the tissue while the cutting edges of the first shell cores tissue at the target site, and wherein the vacuum removes bodily fluids from a vicinity of a distal end of the lateral incision catheter.

6. The catheter according to claim 1, wherein the cutting surfaces of the first and second shells are serrated to aid in cutting through tissue.

7. The catheter according to claim 1, wherein the cutting surfaces further comprise a lubricious material coating to reduce friction to aid in cutting through tissue.

\* \* \* \* \*